United States Patent [19]

Bressler et al.

[11] 3,957,832
[45] May 18, 1976

[54] EPOXY RESINS PREPARED FROM POLYHYDROXY-CONTAINING COMPOUNDS

[75] Inventors: Wilbur L. Bressler; Clyde G. Taylor, both of Lake Jackson, Tex.

[73] Assignee: The Dow Chemical Company, Midland, Mich.

[22] Filed: Dec. 4, 1974

[21] Appl. No.: 529,323

Related U.S. Application Data

[63] Continuation-in-part of Ser. No. 20,011, March 16, 1970, abandoned.

[52] U.S. Cl. .................. 260/348 R; 260/619 B; 260/47 EP
[51] Int. Cl.² ............. C07D 303/26; C07D 303/24
[58] Field of Search ................... 260/348 R

*Primary Examiner*—Norma S. Milestone
*Attorney, Agent, or Firm*—James G. Carter

[57] ABSTRACT

New polyhydroxy-containing compounds represented by the formula

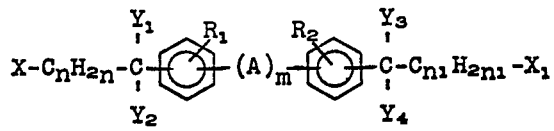

wherein A is —O— or an alkylidene group having 1 to 4 carbon atoms, $Y_1$, $Y_2$, $Y_3$ and $Y_4$ are independently selected from —OH or

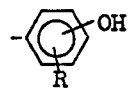

(wherein R is selected from hydrogen, a halogen atom and an alkyl group having 1 to 4 carbon atoms), X and $X_1$ are independently selected from hydrogen, a halogen atom or the group

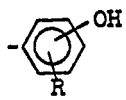

(wherein R is as defined above), $R_1$ and $R_2$ are selected from hydrogen, a hydroxyl group, and an alkyl group having from 1–4 carbon atoms, m is the number 0 or 1 and n and $n_1$ are numbers independently selected from 1 to 20. A process for their preparation is disclosed as well as new epoxy resins prepared therefrom which may be represented by the formula

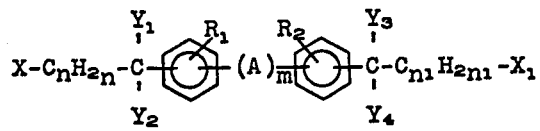

wherein A, m, n, and $n_1$ are defined above and $Y_1$, $Y_2$, $Y_3$ and $Y_4$ are independently selected from —OH and the group

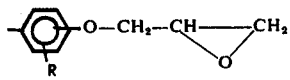

(wherein R is selected from hydrogen, a halogen atom or an alkyl group having from 1 to 4 carbon atoms), $R_1$ and $R_2$ are selected from hydrogen, and alkyl group having from 1 to 4 carbon atoms and the group

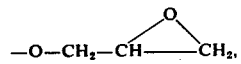

X and $X_1$ are independently selected from hydrogen, a chlorine group and the group

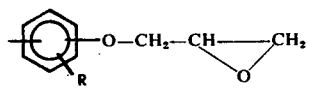

(wherein R is as defined above), m is a number selected from 0 and 1 and n and $n_1$ are numbers independently selected from 1 to 20 wherein at least 2 of the groups selected from $Y_1$, $Y_2$, $Y_3$, $Y_4$, X and $X_1$ are the group

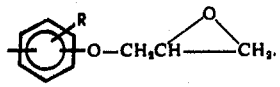

5 Claims, No Drawings

EPOXY RESINS PREPARED FROM POLYHYDROXY-CONTAINING COMPOUNDS

CROSS REFERENCE TO RELATED APPLICATION

This application is a continuation-in-part of application Ser. No. 20,011 filed Mar. 16, 1970 and now abandoned.

BACKGROUND OF THE INVENTION

Industry has been constantly seeking to obtain synthetic resins for use in high temperature applications which are stable at such high temperatures for extended periods of service.

The epoxy resins of the present invention have been found to possess heat distortion temperatures above about 400°F and possess a comparatively high order of stability under prolonged exposures to high temperatures.

SUMMARY OF THE INVENTION

The present invention relates to novel hydroxyl-containing compounds having the general formula

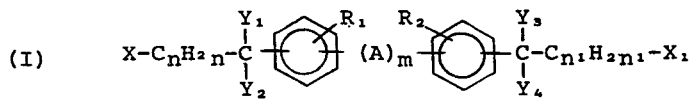

(I)

wherein A is —O— or an alkylidene group having from about 1 to about 4 carbon atoms, $R_1$ and $R_2$ are independently selected from hydrogen, a hydroxyl group, and an alkyl group having from about 1 to about 4 carbon atoms, $Y_1$, $Y_2$, $Y_3$ and $Y_4$ are independently selected from —OH and the group

(wherein R is selected from the group consisting of hydrogen, a halogen atom and an alkyl group having from about 1 to about 4 carbon atoms, X and $X_1$ are independently selected from the group consisting of hydrogen, a halogen atom and the group

(wherein R is as defined above), $m$ is a number selected from 0 to 1 and $n$ and $n_1$ are numbers selected independently from about 1 to about 20, preferably from about 1 to about 4; to a process for their preparation and to novel epoxy resins prepared therefrom which are represented by the general formula

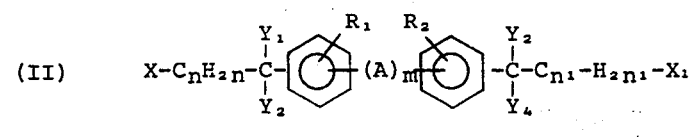

(II)

wherein A is selected from —O— and an alkylidene group having from about 1 to about 4 carbon atoms, $R_1$ and $R_2$ are independently selected from hydrogen and an alkyl group having from about 1 to about 4 carbon atoms, and the group

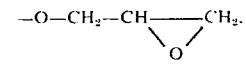

$Y_1$, $Y_2$, $Y_3$, and $Y_4$ are independently selected from —OH and the group

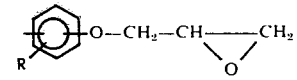

(wherein R is as defined above), X and $X_1$ are independently selected from hydrogen, a halogen atom and the group

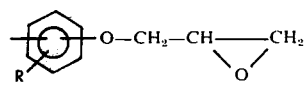

(wherein R is as defined above), and wherein $m$, $n$ and $n_1$ are as defined above and wherein at least 2 of the groups selected from $Y_1$, $Y_2$, $Y_3$, $Y_4$, X and $X_1$ are the group

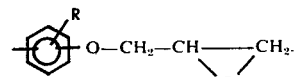

DETAILED DESCRIPTION OF THE INVENTION

The new polyhydroxy-containing compounds of this invention and the epoxy resins prepared therefrom may be prepared by reacting a diphenyl compound with an acylhalide or haloacylhalide in a molar ratio of about 2 moles of acylhalide or haloacylhalide to 1 mole of diphenyl compound in the presence of a Friedel-Crafts catalyst at a temperature in the range of from about 0° to about 10°C for an initial period of reaction ranging from about 2 hours to about 4 hours and then increasing the temperature to about 10°C to about 25°C for a remaining period of time ranging from about 4 hours to about 20 hours at atmospheric pressure. The resultant product is then reacted, in the presence of a mercaptan as a catalyst and optionally in the presence of resorcinol as an additional catalyst, with an excess of a phenolic compound in the presence, initially, of anhydrous HCl at a temperature in the range of from about 25° to about 40°C and preferably from about 33° to about 37°C for a period of time in the range of from about 4 hours to about 72 hours and preferably from about 16 hours to about 24 hours at pressures in the range of from about 1 atm. to about 2 atm. Excess phenolic compound is then removed by a suitable technique such as vacuum stripping or water washing. The resultant product contains a plurality of phenolic hydroxyl groups.

Those skilled in this field will recognize that the products prepared above may be and usually are mixtures of two or more compounds. The compounds so produced will have an average phenolic hydroxyl functionality in the range of at least 2 and usually from about 3 to about 5 and most usually from about 3 to about 4. These usually have melting points in the range of from about 100°C to about 215°C depending upon the residual phenolic compound left in the product. Such polyhydroxy-containing products find utility as intermediates to the preparation of epoxy resins having superior properties.

The epoxy resins of this invention may be prepared by reacting the above prepared polyhydroxycontaining products with an excess of an epihalohydrin in the presence of a basic acting catalyst at temperatures in the range of from about 30° to about 50°C and preferably from about 40° to about 45°C for a period of time ranging from about 48 hours to about 96 hours and preferably from about 60 hrs. to about 72 hrs. The resultant halohydrin ether is then dehydrohalogenated with a suitable alkaline acting material at a temperature of from about 30° to about 35°C and preferably from about 30° to about 35°C for a period of time ranging from about 2 hours to about 4 hours and preferably frm about 3 hours to about 4 hours. The product is then filtered and washed with water. The thus prepared epoxy resin product is actually a mixture of products having a plurality of epoxy groups and usually having an average epoxide functionality in the range of at least 2 and generally from about 3 to about 5 in the form of glycidyl ether groups.

Suitable diphenyl compounds which may be employed in the preparation of the polyhydroxyl-containing compositions of this invention include, for example, biphenyl, diphenyl oxide, di(methylphenyl) oxide, diphenyl methane, di(methylphenyl)methane, p,p'-isopropylidene diphenol and the like.

Suitable acylhalides which may be employed in the preparation of the polyhydroxyl-containing compositions of this invention include, for example, those containing from about 2 to about 20 carbon atoms such as, for example, acetyl chloride, acetyl bromide, propionyl chloride, propionyl bromide, stearoyl chloride, stearoyl bromide, mixtures thereof and the like.

Suitable haloacylhalides which may be employed in the preparation of the compositions of this invention are those containing from about 2 to about 20 carbon atoms which include, for example, chloroacetyl chloride, bromoacetylbromide, chloropropionyl chloride, bormopropionylbromide, chlorostearoylchloride, bormostearoylbromide and the like and mixtures thereof.

Suitable phenolic compounds which may be employed in the preparation of the compositions of this invention include, for example, phenol, methylphenol, ethylphenol, p-tertiarybutylphenol, chlorophenol, bromophenol and the like and mixtures thereof.

Suitable Friedel-Crafts catalysts which may be employed in the reaction between the diphenyl compound and the acylhalide or haloacylhalide include, for example, aluminum trichloride, zinc chloride, stannic chloride, and the like.

Suitable mercaptan catalysts are the alkyl mercaptans containing from about 2 to about 12 carbon atoms including, for example, dodecylmercaptan, ethyl mercaptan, isopropyl mercaptan, sec-butyl mercaptan, n-amyl mercaptan, n-hexyl mercaptan and the like.

In addition to the alkyl mercaptan, resorcinol can be added as an auxiliary catalyst. This usually acts to increase the rate of reaction between the phenol and the diphenyl-acylhalide or haloacylhalide reaction products.

Suitable epihalohydrins which may be employed in the preparation of the epoxy resins of this invention include, for example, epichlorohydrin, epibromohydrin, epiodohydrin and mixtures thereof.

Suitable basic acting catalysts which may be employed in the reaction step between the polyhydroxycontaining compounds of this invention and the epihalohydrin include, for example, tertiary amines such as, for example, N-methyl morpholine, trimethyl amine and the like, onium salts of nitrogen, phosphorus and sulfur, such as, for example, benzyl trimethylammonium chloride, ethyltriphenyl phosphonium iodide, triphenyl sulfonium chloride and the like.

Suitable alkaline acting materials which may be employed in the dehydrohalogenation reaction include, for example, sodium hydroxide, potassium hydroxide, sodium and potassium carbonates and the corresponding bicarbonates, the hydroxides of magnesium, zinc, lead, iron, aluminum and the like as well as aluminates, silicates and zincates of alkali metals. Preferably, an aqueous solution of a mixture of sodium hydroxide and sodium carbonate is employed.

Suitable curing agents which may be employed with the epoxy resins of this invention to form insoluble, infusible thermoset resins include, for example, aliphatic and aromatic amines such as, for example, metylenedianiline, metaphenylenediamine, diethylenetriamine, triethylenetetraamine, tetraethylenepentamine, mixtures thereof and the like; anhydrides such as for example, tetrahydrophthalic anhydride, hexahydrophthalic anhydride, Nadic methyl anhydride, benzophenone tetracarboxylic dianhydride, trimellitic anhydride, pyromellitic dianhydride, mixtures thereof and the like; and latent curing agents such as, for example, dicyandiamide, borontrifluoride complex with monoethanol amine, boron trifluoride complex with mekamine, mixtures thereof and the like.

The conditions necessary to initiate curing of the epoxy resins of this invention depend upon the particular curing agent chosen. Those skilled in the art are familiar with the particular conditions suitable for curing an epoxy resin with a particular curing agent. Chapters 5 thru 12 of *HANDBOOK OF EPOXY RESINS*, McGraw Hill Book Co., 1967, by Henry Lee and Kris Neville discuss the various curing agents, mechanisms and conditions for cure for various types of curing agents. Generally, from about 0.9 to about 1.1 stoichiometric equivalents per epoxy equivalent are employed.

The epoxy resins of this invention may be blended with inert fillers, such as clay, asbestos, silica, metal powders, chopped fiberglass, calcium carbonate, carbon black and the like.

The epoxy resins of this invention may also be mixed with various reactive diluents, flexiblizers, extenders, solvents and the like.

The novel epoxy resins of this invention may be employed, with the appropriate curing and/or accelerating compounds, as coatings (including fluid bed and solvent born), castings, adhesives, encapsulants for electrical components, such as resistors, transistors, condensers, motor windings and the like, and are particularly suited for use in transfer molding processes.

The reactions employed in preparing the products to the present invention produce mixtures of products which are represented by the following reaction scheme employing diphenyl oxide as the diphenyl compound and chloroacetylchloride as the haloacyl halide and phenol as the phenolic compound.

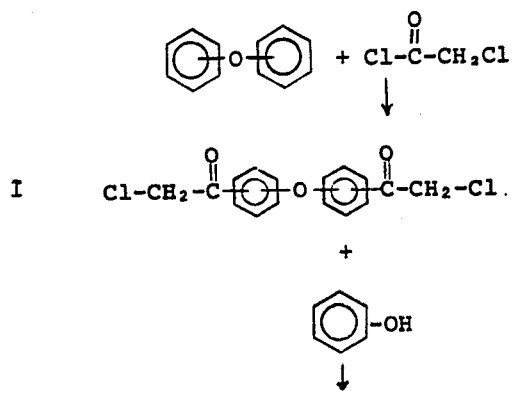

A mixture of the following products having an average phenolic hydroxyl functionality of at least 3

Epoxy resins are then prepared by reacting the phenolic hydroxyl groups of the mixture of products with an epihalohydrin followed by dehydrohalogenation to produce a mixture of epoxy resins having an average epoxide functionality of from about 3 to about 4. The mixture would then contain such compounds as represented by the following:

IV-A 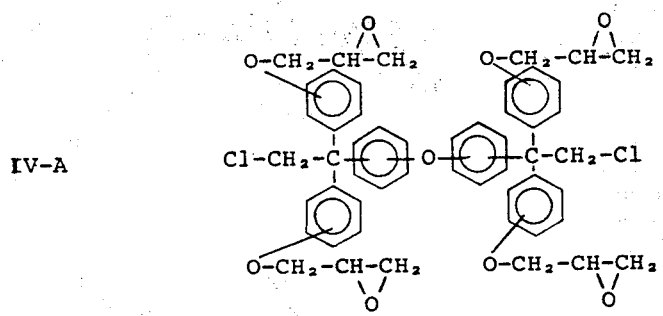
V-A 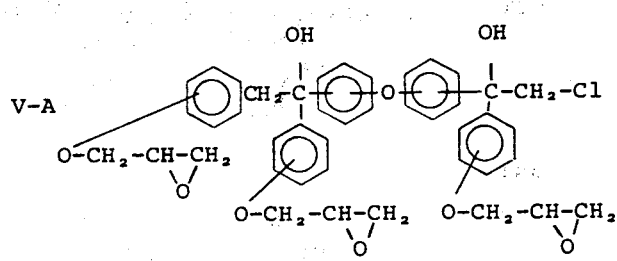
VI-A 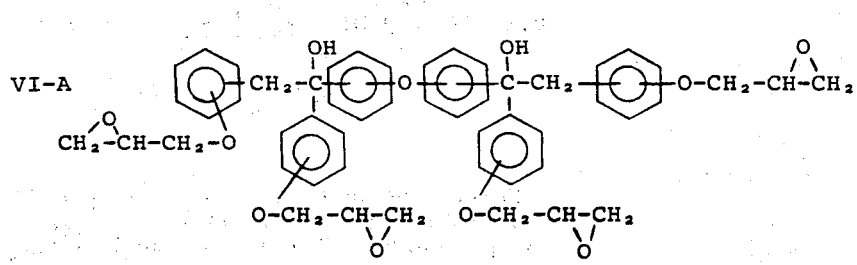
VII-A 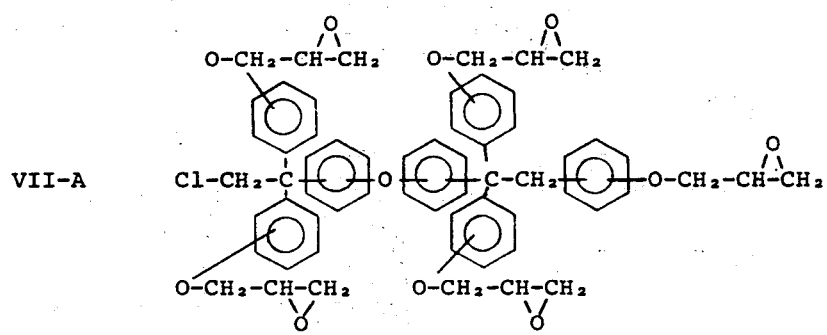
and
VIII-A 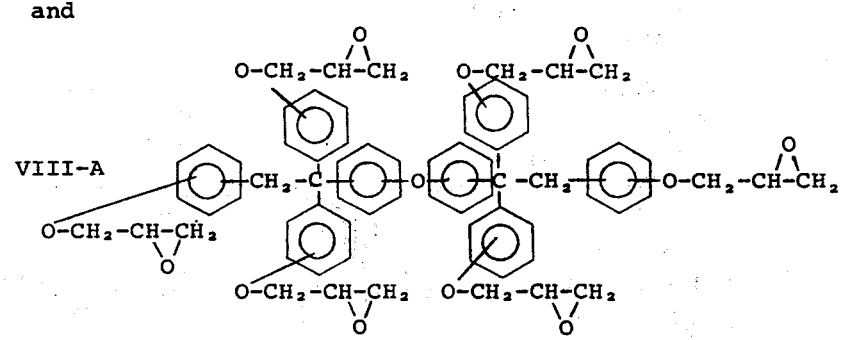

The following examples are provided to more fully illustrate the invention but are not meant to be limiting in any way to the scope of the invention.

EXAMPLE 1

A. Preparation of 4-4'-Oxydiacetophenone

To a 30-gallon glass-lined reaction vessel equipped with an agitator and various inlet ports to accomodate the addition of reactants and stripping of products was added 33.5 lbs. of methylene chloride and 29.34 lbs. of anhydrous aluminum chloride. After cooling the mixture to 0°C, 17.27 lbs. (0.22 moles) acetylchloride was slowly added over a 20-minute period at a temperature of from 0° to 12°C. After stirring at 0°–12°C for 30 minutes, a mixture of 17.02 lbs. (0.10 mole) diphenyl oxide in 5 lbs. of methylene chloride was added over a period of 1 hour at 0°–8°C. After adding 35 lbs. more of methylene chloride, the temperature was maintained between 8°–18°C for 18 hours. After adding an additional 30 lbs. of methylene chloride, the contents were transferred to a 50-gallon stainless steel reactor containing 150 lbs. of water cooled to 0°C. The transfer was conducted over a 1 hour period. The product was then washed 5 times with 100 lb. portions of water to a pH of about 7. After discarding the aqueous layer from the last wash, the methylene chloride was then removed from the organic layer containing the product by stripping for 2 hours at 130°C and 50 mm Hg.

B. Preparation of Phenol-4,4'-Oxydiacetophenone Condensation Product

To a 3-liter, 3-necked flask equipped with a stirrer, thermometer, sparge tube, heating means and condenser was charged 229.08 grams (0.90 mole) 4,4'-oxydiacetophenone, 1686.0 grams (17.91 moles) phenol and 10.08 grams (0.090 mole) resorcinol as catalyst. The mixture was warmed to 50°–55°C in order to dissolve the solids. After cooling to 35°C, 21.36 grams of 1-dodecanethiol catalyst was added and anhydrous HCl was sparged into the mixture for about 1 hour. The flask and its contents were then placed in a 36°C oven for the remainder of the reaction time, about 18 hours. The HCl gas and water were then removed by means of an aspirator vacuum and the excess phenol was removed by means of a vacuum pump at 220°C and <0.1 mm Hg vacuum. About 493 grams of a dark colored product having a melting point in the range of 130°–140°C was recovered. A gel permeation chromatography analysis of the thus prepared polyhydroxyl-containing product revealed such product to contain an average phenolic hydroxyl functonality of about 3–3.5.

C. Epoxidation of Phenol-Oxydiacetophenone Product

Into a 5-liter, 5-necked flask equipped with a drain opening in the bottom, stirrer, condenser and thermometer with temperature controller was charged about 493 grams of the product from B above and 2290 grams of epichlorohydrin. The product was warmed slightly to dissolve the product from B in the epichlorohydrin and then the temperature was raised to 45°C and 9.35 ml of a 60% aqueous solution of benzyltrimethylammonium chloride was added. The reaction was maintained at 45°C for a period of about 65.5 hours. To the thus prepared addition product was added 914 grams of an aqueous solution containing 15.75% NaOH and 9.25% Na$_2$CO$_3$. The temperature was maintained at 35°C for about 2 hours. About 1-1/2 liters of water was then added as an aid in separation. The aqueous layer was separated from the organic layer by withdrawing the organic layer via the drain opening in the bottom of the flask and retaining it and then withdrawing the aqueous layer via the same means and discarding it. The organic layer was then returned to the flask and another 914 grams of the NaOH/Na$_2$CO$_3$ solution was added. The temperature was not controlled during this period, and the temperature rose from 28°C to 36°C after a period of about 1¼ hours. The layers were allowed to separate and the organic layer was washed several times with distilled water until a pH of about 7 was attained. The excess epichlorohydrin was then removed by heating under vacuum. About 593 grams of a product melting in the range of 63° to 68°C and having an epoxide content of 19.42% was recovered. Gel permeation chromatography analysis of the product revealed it to contain an average epoxide functionality of about 3–3.5.

D. Curing of C above

A mixture of 400 grams of the product from C above and 88.44 grams of methylene dianiline was prepared by blending together the above quantities of compounds which were heated separately to a temperature of 120°C. Tensile test specimens were cast using the resultant mixture. The specimens were then cured for 16 hours at 70°C, 2 hours at 125°C and 2 hours at 175°C. The specimens were then tested at room temperature and at 200°C using an Instron machine with a D-cell and a speed setting of .2 inches per minute. The results of an average of 3 specimens are given below:

|  | Room Temp. | 200°C |
|---|---|---|
| Tensile Strength | 4540 psi | 3837 psi |
| % Elongation | 2.1% | 3.6% |

EXAMPLE 2

A. Preparation of Bis(4-Chloroacetylphenyl)Ether

To a 3-liter, 3-necked reaction flask, placed in an ice-salt bath and fitted with stirrer, thermometer, and addition funnel, was added 580 grams (4.33 moles) anhydrous aluminum chloride, 500 ml. methylene chloride solvent and 434.0 grams (3.8 moles) chloroacetyl chloride. The contents were cooled to 0°C and 294.5 grams (1.73 moles) of phenyl ether (diphenyl oxide) dissolved in 100 ml methylene chloride was slowly added over a period of 2 hours with care being taken to maintain the temperature below 10°C. Upon completion of the phenyl ether addition, the contents were maintained at about 10°C for an additional period of about 2 hours. The contents were then allowed to rise to a temperature of 20°–25°C and left overnight while stirring. The contents were then raised to 45°C and maintained thereat for about 1 hour. The Friedel-Crafts catalyst was then inactivated by pouring the solution into a beaker containing ice and hydrochloric acid. The product was then extracted with methylene chloride and washed several times with water, 2 washes of which contained NaHCO$_3$, until a pH of about 7 was attained. The majority of solvent was then removed with a steam bath and the residual traces of solvent were removed in a vacuum oven at 105°–110°C. The dark brown product had a melting point of about 75°–80°C.

B. Preparation of Phenol-Oxydichloroacetophenone Condensation Product

To a 5-liter, 3-necked flask, equipped with stirrer, thermometer, temperature control means, and nitrogen purge was added 323.2 grams (1.0 mole) of the product prepared in A above; 2823.3 grams (30.0 moles)

phenol, 11.0 g. (0.1 mole) resorcinol and 20.0 grams dodecyl mercaptan. The mixture was stirred while warming until all of the contents went into solution. Anhydrous HCl was then sparged into the solution for 30-45 minutes to completely saturate the solution. The flask was then stoppered and placed in a 36°C oven for a period of about 63.5 hours. The HCl and water were then removed by means of an aspirator vacuum and the phenol removed under 3.0 mm Hg vacuum at a maximum temperature of about 215°C pot temperature. About 708 grams of a dark brown solid product melting in the range of 164°–175°C and a total chloride content of 0.16% was recovered. Analysis by Gel Permeation Chromatography revealed the product to contain an average phenolic hydroxyl functionality of about 4.

C. Epoxidation of Phenol-Oxydichloroacetophenone Product

To a 3-liter, 3-necked flask equipped with stirrer, thermometer, condenser, temperature control means, and nitrogen purge was added 350 grams (about 0.45 mole) of the product prepared in B above and 1250 grams (13.5 moles) of epichlorohydrin. The mixture was stirred and armed until all the contents went into solution. The temperature was raised to 45°C and 6.1 grams of a 60% aqueous solution of benzyltrimethylammonium chloride was added. The contents were maintained at 45°C for about 63 hours. The contents were then washed twice with 457 grams of an aqueous solution containing 15.75% NaOH and 9.25% $Na_2CO_3$ for 2 hours. The First wash was conducted at 35°C and the second at 30°C. The aqueous layer was separated and discarded and the organic layer was washed several times with distilled water until a pH of about 7 was reached and a negative test for $Cl^-$ was obtained. The $Cl^-$ test was conducted by acidifying a small portion of the water layer with nitric acid and checking for a white silver chloride precipitate upon the addition of a few drops of silver nitrate solution. About 200 grams of epichlorohydrin was added during the washing step to aid in the extraction of the product. The epichlorohydrin was then removed by means of a vacuum at 0.5–1.0 mm Hg and a pot temperature of 215°C. About 446 grams of a dark brown product having a melting point range of 93°–100°C and an epoxide content of 19.52% was obtained. The product also had a phenolic OH content of 0.21%, a total chloride content of 0.44% and a hydrolyzable chloride content of 0.21%. Gel permeation chromatography analysis of the product revealed it to contain an average epoxide functionality of about 4.

D. Spiral Flow Testing of C Above

The product from C above was then formulated for spiral flow testing employing the following receipe:

25.0 grams product from C above
5.61 grams methylenedianaline
20.0 grams ASP-400 clay
1.0 gram zinc stearate
0.75 gram resorcinol When tested according to the procedure given in *MODERN PLASTICS*, Feb. 1968, pages 104–108, using 20 grams of the above formulation at 300°F and 1000 psi, the above formulation had a spiral flow of 63 inches.

Approximately 100 grams of the product from D above was cured with 30 grams of methylenedianiline at 70°C for 16 hours, 125°C for 2 hours and finally at 175°C for 2 hours. The heat distortion temperature of the cured specimen was >265°C when tested by the procedure of ASTM D-648-56.

EXAMPLE 3

A. Preparation of 4,4'-Oxydiacetophenone
   Same as in Example 1-A.

B. Preparation of Phenol-Oxydiacetophenone Condensation Product

Into a 1-liter, 5-necked flask equipped with stirrer, thermometer, sparge tube, heating means, and condenser was charged 76.36 grams (0.30 mole) of the product from Example 1-A, 562.0 grams (5.97 moles) phenol, and 3.36 grams (0.03 moles) resorcinol. The contents were warmed in order to get all the materials into solution. After cooling to 30°C, 7.12 grams of dodecylmercaptan was added. Anhydrous HCl was then sparged into the solution for about 15 minutes The contents exothermed to a temperature of 37°C. The solution was then transferred to a 16 oz. bottle and placed in a 36°C oven for 22 hours The contents were then transferred to a 500 ml flask and the excess phenol removed at 0.5–1.0 mm Hg and a pot temperature of 230°C. About 164 grams of a dark brown solid product having a melting point of 135°–150°C was recovered. Analysis by Gel Permeation Chromatography revealed the product to contain an average phenolic hydroxyl content of about 3.0–3.2.

C. Epoxidation of Phenol-oxydiacetophenone Condensation Product

Into a 2-liter, 3-necked flask equipped with stirrer, thermometer, temperature control means, nitrogen purge means and condenser was placed 164 grams of the product from B above and 638 grams of epichlorohydrin. The contents were warmed to dissolve the product from B above in the epichlorohydrin. The temperature was raised to 45°C and 3.13 ml of a 60% aqueous solution of benzyltrimethylammonium chloride was added. The temperature was controlled at 45°C for 2½ days. The product was cooled to 35°C and 437 grams of an aqueous caustic-carbonate solution (15.75% NaOH-9.25% $Na_2CO_3$). The contents were maintained at 35°C for 2 hours. The aqueous layer was then removed and the organic layer treated with another 437 gram quantity of the caustic-carbonate solution at 35°C for 2 hours. Since material was quite viscous, 150 ml of epichlorohydrin and 129 ml toluene was added. The aqueous layer was removed and the organic layer was treated with 250 ml of distilled water. A product layer and an emulsion layer resulted. The product layer was separated and the emulsion layer was left standing overnight. The product which separated from the emulsion during the night was then added to the original portion of the product and washed 7 times with 750 ml portions of distilled water. About 193 grams of a dark brown solid product having an epoxide content of 19.75% and a melting point of 65°–69°C was recovered. Analysis by Gel Permeation Chromatograhy revealed the product to contain an average epoxide functionality of about 3.2–3.5.

D. Curing of C above

Heat distortion bars werre cast in a mold preheated to 55° from a mixture obtained by mixing at 120°C, 22 grams of methylene dianiline and 100 grams of the product from C above. The bars were heated at 70°C for 16 hours, 125°C for 2 hours and 175°C for 2 hours. The heat distortion temperature of the samples were evaluated according to ASTM D 648-56. The heat distortion temperature of the sample was 259°C.

EXAMPLE 4

A. Preparation of 4,4'-Oxydiacetophenone
To a 3-liter, 3-necked flask equipped with a stirrer, thermometer, nitrogen purge means, addition funnel and condenser was added 293.4 grams (2.20 moles) anhydrous aluminum trichloride, 250 ml methylene chloride and 157.0 grams (2.0 moles) acetyl chloride. The solution was cooled to 0°–5°C and 170.2 grams (1.0 mole) diphenyl oxide dissolved in 75 ml methylene chloride was added dropwise over a 45–60 minute period. The contents were allowed to react overnight, while the temperature rose to 20°C. The solution was then poured over ice containing a quantity of concentrated hydrochloric acid to neutralize the catalyst. The product was extracted with methylene chloride. The methylene chloride was removed by evaporation on a steam bath. The product was recrystallized from isopropanol. A tan solid product in the amount of 202 grams was recovered which had a melting point of 101°–102°C.

B. Oxydiacetophenone-Phenol Condensation Product

To a 3-liter, 3-necked flask equipped with a stirrer, thermometer, HCl sparge tube and condenser was added 76.36 grams (0.30 mole) of the product from A above, 564.66 grams (6.0 moles) phenol, 200 ml of glacial acetic acid as a solvent and 7.12 grams of dodecylmercaptan. The contents were cooled to 0°–5°C and anhydrous HCl was sparged into the solution until it appeared to be saturated with HCl. The contents were allowed to react for about 59.5 hours during which time, the temperature rose to 20°C. The product solution was washed with hot water until a yellow-orange granular material formed and then the granular material was washed twice with methylene chloride. The product was filtered and washed twice with hot water, ground in a Waring Blender, filtered and dried in a 160°C oven. A reddish-orange solid product in the amount of 152 grams was recovered which had a melting point of 194°–198°C.

Analysis of the product by Gel Permeation Chromatography revealed it to contain an average phenolic hydroxyl functionality of about 3.0–3.2.

C. Epoxidation of Phenol-Oxydiacetophenone Product

To a 2-liter, 5-necked flask equipped with stirrer, thermometer, a nitrogen purge means, and condenser was added 150 grams of the product from B above and 585 grams of epichlorohydrin. The contents were warmed to dissolve the solid product from B in the epichlorohydrin. The temperature was then raised to 45°C and 2.86 ml of a 60% aqueous solution of benzyltrimethylammonium chloride catalyst was added and the temperature was maintained at 45°C for about 68.5 hours. After cooling to 40°C, 400 grams of an aqueous caustic-carbonate solution (15.75% NaOH-9.25% $Na_2CO_3$) was added and the temperature was maintained at 40°C for 2 hours. The contents were then transferred to a separatory funnel and a small undetermined quantity of toluene was added to aid separation. The organic layer was then recovered and returned to the flask where an additional 400 grams of the caustic-carbonate solution was added. The temperature was again maintained at 40°C for 2 hours.

The organic layer was recovered and washed with water until a negative test for $Cl^-$ was observed by acidifying 2–5 ml of the water layer with dilute nitric acid and observing whether a silver chloride precipitate formed after adding silver nitrate solution.

The solution was dried with $CaSO_4$ and toluene and the unreacted epichlorohydrin was removed by flashing at 1 mm Hg and a pot temperature of 210°C. A brown solid product in the amount of 172 grams was recovered which had a melting point of 72°–74°C and an epoxide content of 19.64%. Gel permeation chromatography revealed the product to have an average epoxide functionality of about 3.0–3.2.

D. Curing of C Above

The product from C above was then cured employing 100 grams of C and 21.1 grams of methylene dianiline and heating for 16 hours at 70°C, 2 hours at 125°C and finally 2 hours at 175°C.

The cured sample was then subjected to an isothermal weight loss test at 260°C by placing the test samples (½ × ½ × ¼ inch) in the oven, periodically removing and weighing them, and calculating the percent weight loss.

The results are given in Table I.

For comparative purposes, two commercially available epoxy resins described below were cured with the same curing agent and cure schedule as that of Example 4-D above and subjected to the same isothermal weight loss test as that of Example 4-D. These results are also given in Table I.

Resin A (The epoxidized product of a phenol/glyoxal condensation product having a % epoxide of 18.33 commercially available from HYSOL Corp. as HYSOL R-2160), 100 grams was cured with 21.1 grams of methylenedianiline.

Resin B (The glycidyl ether of a tertiarybutylphenol/formaldehyde condensation product having a % epoxide of 19.3 designated by The Dow Chemical Co. as DEN 445), 100 grams, was cured with 22.2 grams of methylene dianiline.

TABLE I

| Cured Resin Product | Percent Weight Loss at 260°C After The Indicated Number of Hours | | | | | | |
|---|---|---|---|---|---|---|---|
| | 25 | 50 | 91 | 135 | 183 | 230 | 316 |
| Ex. 4-D | 0.98 | 2.59 | 7.04 | 8.58 | 9.24 | 9.67 | 10.11 |
| A | 9.57 | 11.12 | 12.38 | 13.61 | 14.68 | 15.73 | 16.18 |
| B | 6.91 | 7.83 | 9.44[1] | 11.15[2] | 12.89[3] | 13.57[4] | 1.61[5] |

[1] After 71 hours
[2] After 136 hours
[3] After 187 hours
[4] After 229 hours
[5] After 348 hours The data in the above table clearly demonstrates the superior high temperature stability of the products of this invention.

In a manner similar to the foregoing examples, biphenyl, diphenylmethane, p,p'-isopropylidene diphenol, propionylchloride, butyl chloride, bromophenol, chlorophenol and methyl phenol can be employed as reactants to produce novel polyhydroxyl containing compounds and novel epoxy resins having substantially like properties.

We claim:
1. An epoxy resin mixture having the formula

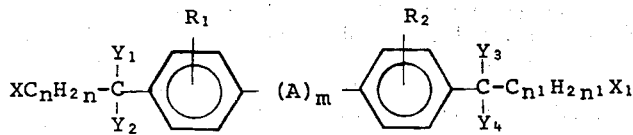

wherein $R_1$ and $R_2$ are hydrogen, A is —O—, $Y_1$, $Y_2$, $Y_3$, and $Y_4$ are independently selected from the group consisting of OH and

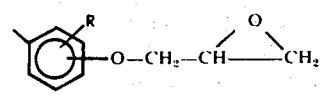

wherein R is hydrogen, X and $X_1$ are independently selected from the group consisting of hydrogen, a halogen and

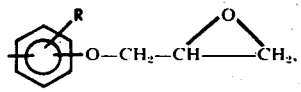

$m$, $n$ and $n_1$ are 1 and wherein an average of from about 3 to about 4 of the groups selected from $Y_1$, $Y_2$, $Y_3$, $Y_4$, X and $X_1$ are the group

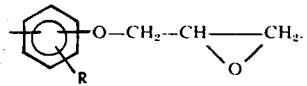

2. An epoxy resin mixture of claim 1 wherein X and $X_1$ are hydrogen.

3. An epoxy resin of claim 1 wherein X and $X_1$ are the group

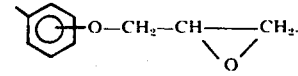

4. An epoxy resin mixture of claim 1 wherein X and $X_1$ are hydrogen and wherein the average epoxide functionality as determined by gel permeation chromatography is in the range of from about 3 to about 3.5.

5. An epoxy resin mixture of claim 1 wherein X and $X_1$ are selected from chlorine and the group

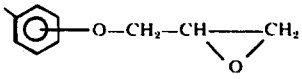

and wherein the average functionality as determined by gel permeation chromatography is about 4.

* * * * *